(12) United States Patent
Denton et al.

(10) Patent No.: US 6,628,398 B1
(45) Date of Patent: Sep. 30, 2003

(54) TONER PATCH SENSOR WITH INTEGRATING OPTICAL COLLECTION GEOMETRY

(75) Inventors: Gary Allen Denton, Lexington, KY (US); Wilson Morgan Routt, Jr., Lexington, KY (US)

(73) Assignee: Lexmark International, Inc., Lexington, KY (US)

(*) Notice: Subject to any disclaimer, the term of this patent is extended or adjusted under 35 U.S.C. 154(b) by 82 days.

(21) Appl. No.: 09/704,133

(22) Filed: Nov. 1, 2000

(51) Int. Cl.[7] .................... G01N 21/55; G01N 21/47
(52) U.S. Cl. ........................... 356/445; 356/446
(58) Field of Search ..................... 356/445, 446, 356/236; 399/30, 49; 250/228

(56) References Cited

U.S. PATENT DOCUMENTS

| | | |
|---|---|---|
| 4,277,162 A | 7/1981 | Kasahara et al. |
| 4,345,835 A * | 8/1982 | Kramer et al. ............... 347/112 |
| 4,487,504 A | 12/1984 | Goldsmith |
| 4,550,998 A | 11/1985 | Nishikawa |
| 4,651,088 A | 3/1987 | Sawada |
| 4,951,088 A | 8/1990 | Bonvallet et al. |
| 4,989,985 A | 2/1991 | Hubble, III et al. |
| 5,083,161 A | 1/1992 | Borton et al. |
| 5,224,714 A | 7/1993 | Kimura et al. |
| 5,244,714 A * | 9/1993 | Malhotra et al. ............ 428/195 |
| 5,313,252 A | 5/1994 | Castelli et al. |
| 5,512,986 A | 4/1996 | Toyomura et al. |
| 5,517,315 A | 5/1996 | Snail et al. |
| 5,530,530 A | 6/1996 | Tanaka et al. |
| 5,537,203 A | 7/1996 | Carr |
| 5,666,194 A | 9/1997 | Denton |
| 5,722,009 A | 2/1998 | Haneda et al. |
| 5,745,234 A | 4/1998 | Snail et al. |
| 5,761,570 A | 6/1998 | Sawayama et al. |
| 5,859,709 A * | 1/1999 | Imura ......................... 250/228 |
| 5,887,223 A | 3/1999 | Sakai et al. |
| 5,912,741 A * | 6/1999 | Carter et al. ................. 356/445 |
| 5,933,680 A | 8/1999 | Nishimura |
| 5,940,654 A | 8/1999 | Uchiyama et al. |

* cited by examiner

Primary Examiner—Zandra V. Smith
(74) Attorney, Agent, or Firm—John A. Brady; Ronald K. Aust; Taylor & Aust, P.C.

(57) ABSTRACT

A toner patch sensor arrangement in an electrophotographic machine includes a substantially hollow chamber having a reflective interior surface, a first opening exposing a toner patch, a second opening and a third opening. A light emitting element emits light onto the toner patch through the first opening and the second opening. A light detecting element receives through the third opening light reflected off of the toner patch such that the reflected light is received only after the light has also reflected off the interior surface of the chamber.

27 Claims, 3 Drawing Sheets

TONER PATCH SENSOR WITH INTEGRATING OPTICAL COLLECTION GEOMETRY

BACKGROUND OF THE INVENTION

1. Field of the Invention

The present invention relates to monitoring toner density of an unfused image in an electrophotographic machine, and, more particularly, to a toner patch sensor arrangement for monitoring toner density of an unfused image in an electrophotographic machine.

2. Description of the Related Art

Toner patch sensors are used in printers and copiers to monitor the toner density of unfused images and provide a means of controlling the print darkness. In color printers and copiers, the toner patch sensors are used to maintain the color balance and in some cases to modify the gamma correction or halftone linearization as the electrophotographic process changes with the environment and aging effects. It is a known problem that conventional reflection-based toner patch sensors will lose their calibration if the toner bearing surface changes in how the light is absorbed and scattered due to wear or toner filming.

Conventional reflection-based toner sensors use a single light source to illuminate a test patch of toner. In most cases the density of the toner patches are sensed on the photoconductor. With the advent of color laser printers with intermediate transfer belts, it is known to sense toner patches on the intermediate transfer medium rather than on the photoconductor surfaces. Toner patch sensing on the four photoconductor drums can be an unattractive option since it requires four sensors, and there may be no room for four such sensors between the cartridge and the intermediate belt.

It is known to use reflection signal ratios as opposed to differences in the toner patch signals. In a ratio control system, the reflectivity of a toner-free surface is sensed and compared to the reflectivity of the toned patch. By taking the ratio of these two signals, signal variations due to the variations in the light source, the detector, and the relative positions of these elements cancel out. However, this method of image density control is not self-compensating for degradation of the toner bearing surface, such as the photoconductive drum or intermediate belt, due to wear or toner filming.

Similar methods of maintaining accurate density control include sensing special toner patches with "saturated" toner densities. Saturated patches on an intermediate surface can be sensed, and the resulting values can be used for density control and gradation correction.

Intermediate belts are prone to toner filming and mechanical wear. Since changes in the surface roughness of the intermediate belt will affect the amount of light that is scattered at the belt surface and the direction in which the light is scattered, the toner patch sensor needs to be made insensitive to the surface roughness of the intermediate belt surface.

What is needed in the art is a toner patch sensor arrangement that can accurately measure the toner thickness on a surface having various degrees of surface roughness.

SUMMARY OF THE INVENTION

The present invention provides a method of maintaining accurate density control independent of the intermediate belt surface roughness.

The invention comprises, in one form thereof, a toner patch sensor arrangement in an electrophotographic machine. A substantially hollow chamber has a reflective interior surface, a first opening exposing a toner patch, a second opening and a third opening. A light emitting element emits light onto the toner patch through the first opening and the second opening. A light detecting element receives through the third opening light reflected off of the toner patch such that at least a majority of the reflected light is received only after the light has also reflected off the interior surface of the chamber.

An advantage of the present invention is that toner thickness can be accurately measured on a surface having various degrees of surface roughness.

Another advantage is that only one photosensitive device is needed.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate one preferred embodiment of the invention, in one form, and such exemplifications are not to be construed as limiting the scope of the invention in any manner.

DETAILED DESCRIPTION OF THE INVENTION

Figure 1:
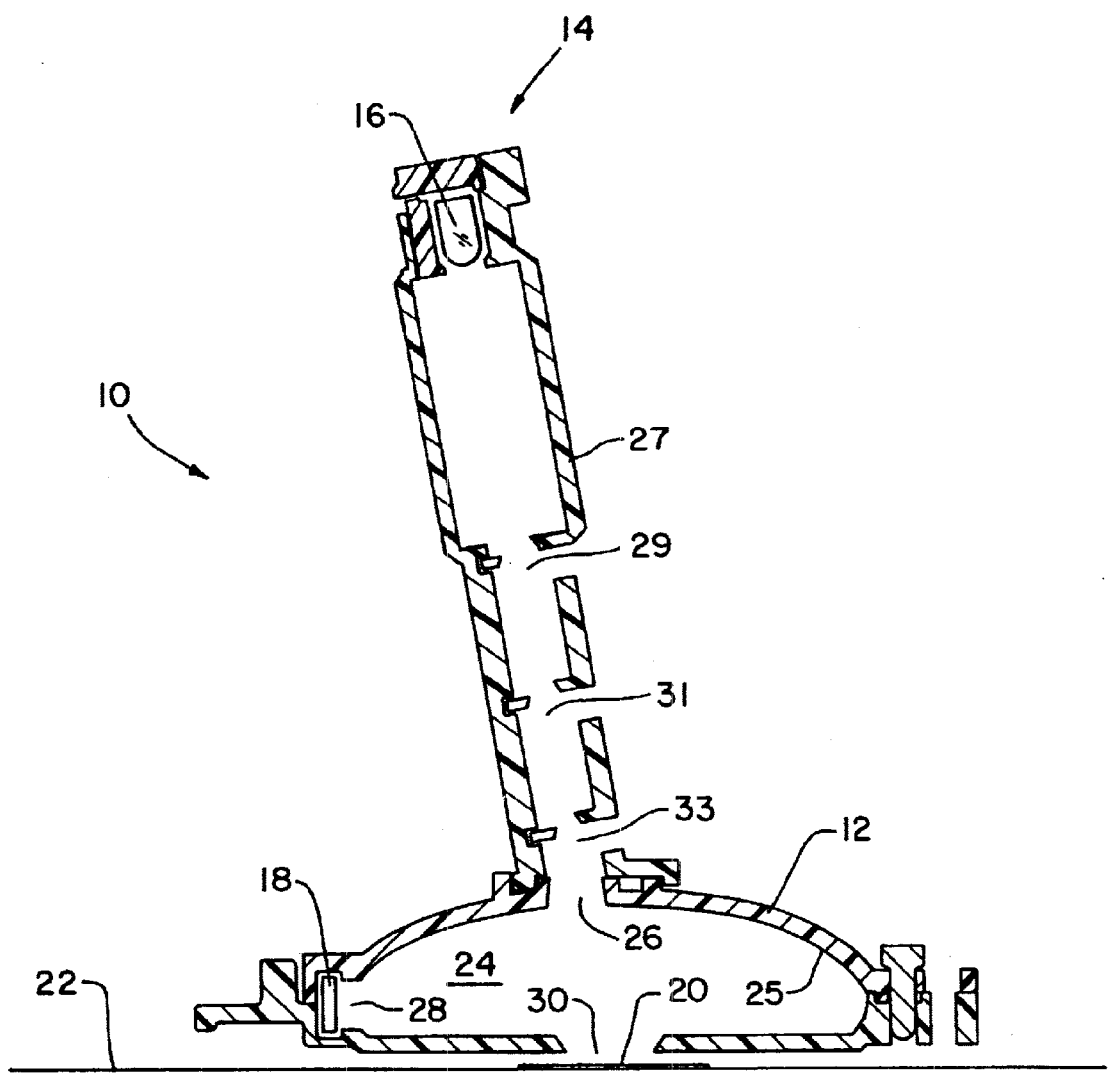
FIG. 1 is a side, sectional view of a first embodiment of a toner patch sensor arrangement of the present invention.

Referring now to the drawings, and, more particularly to FIG. 1, there is shown one embodiment of a toner patch sensor arrangement 10 of the present invention, including a reflective chamber 12 and a toner patch sensor 14.

A single toner patch sensor 14, including an infrared light emitting diode 16 and a silicon photosensitive diode 18, is used to measure a toner patch 20 that has been developed and transferred to an intermediate transfer belt 22. Sensor arrangement 10 is positioned in close proximity to an intermediate belt drive roll (not shown), after the last color transfer station (not shown). Light emitting diode 16 can have a narrow output beam, such as that of diode SFH480 produced by Infineon.

Chamber 12 includes an integrating optical cavity 24 which allows photosensitive diode 18 to detect light reflected off the surface of belt 22 at multiple angles of incidence and/or reflection, thereby providing toner patch sensor 14 with a high level of accuracy. Chamber 12 may have the shape of a box, cylinder, sphere or other hollow three-dimensional volume. Chamber 12 may be molded from a thermoplastic such as polystyrene which has been loaded with titanium dioxide to produce a high reflectivity, such as SC24-244 from RTP Imagineering Plastics. Because light may undergo multiple reflections inside chamber 12 before it reaches photodiode 18, the reflectivity of cavity 24 can be above 90%.

Alternatively, chamber 12 can be formed of a material having low surface reflectivity, and an inside surface 25 that defines cavity 24 of chamber 12 can be coated with barium sulfate to create a highly reflective but non-specular surface.

Chamber 12 includes openings 26, 28 and 30 associated with the illumination source 16, the photodiode 18, and the test patch 20, respectively. Light source 16 is disposed in a collimating unit 27 molded from polycarbonate loaded with 2%–3% carbon black to produce a highly absorptive material at the wavelength of emitter 16. Collimating unit 27 has three apertures 29, 31 and 33 which are disposed between emitter 16 and entry aperture 26. Apertures 29, 31, 33 serve to define the extent and direction of the light beam so that it can pass through entry aperture 26 and sampling aperture 30 without reflecting off either of the surfaces surrounding apertures 26 and 30.

In the embodiment of FIG. 1, openings 26, 28 and 30 are configured to allow direct illumination with indirect detection. More particularly, the illuminating light from light emitting diode 16 enters reflective cavity 24 through a small opening 26 and most or all of the light reflects off the surface of test patch 20 before undergoing further reflections off of interior surface 25 of chamber 12. Entrance aperture 26 is positioned off-center relative to the location of test patch 20 so that any specularly reflected light is diffusely reflected by interior surface 25 of chamber 12 rather than passing immediately back out entrance aperture 26.

Opening 30, through which test patch 20 is illuminated, is in the form of a circular aperture located about 1.5 mm from the surface of intermediate belt 22. The diameter of aperture 30 is approximately 8 mm, which is much larger than the 1.5 mm gap between aperture 30 and the surface of intermediate belt 22. This arrangement ensures that most of the light that is reflected by belt 22 or toner patch 20 will re-enter optical cavity 24 where it can be detected by photodiode 18.

The size and locations of the three apertures 26, 28 and 30 influence to what extent sensor 14 is affected by changes in the surface roughness. The geometry described above was selected based on computer simulation of light reflected off the surface of intermediate belt 22 and interior surface 25 of chamber 12. Calculations were performed using OptiCAD ray tracing software to compare the amount of light detected from a highly specular surface and from a non-specular surface. The computer simulation indicated that differences in the detected light intensity were minimized for this combination of cavity geometry, hole sizes, and hole locations.

Photodiode 18 is placed behind aperture 28 to sample the light intensity in optical cavity 24. Photodiode 18, made by UDT Sensors, Inc. of Hawthorne, Calif., has a relatively large surface area (4 mm×4 mm) and a wide angular sensitivity (+/−40 degrees). The large surface area increases the fraction of the light that is detected by photodiode 18 before it is either absorbed by interior surface 25, or exits cavity 24 through aperture 30 or aperture 26. In the embodiment of Fig. 1, test patch 20, whether bare or toned, is illuminated at a well defined angle of incidence and the reflectance is sensed over a wide range of reflection angles by photodetector 18. Arrangement 10 is relatively insensitive to variations in the roughness of the belt surface because cavity 24 samples the light from many reflected light directions, not just one.

In a second embodiment, toner patch sensor arrangement 32 (FIG. 2), the illuminating light enters optical cavity 24 through a small aperture 26 and is diffusely reflected by interior cavity surface 25 before reaching test patch 20. A small opaque baffle 34 protruding from a lower chamber wall 36, intersecting an imaginary line between light emitting diode 16 and test patch 20, serves to block direct exposure of photodiode detector 18 to the light from light emitting diode 16. A circular opaque flange 37, intersecting an imaginary line between light emitting diode 16 and test patch 20, and also intersecting an imaginary line between test patch 20 and photodiode 18, surrounds and defines opening 30. This second embodiment produces a diffuse illumination of test patch 20. The light reflected by test patch 20 also undergoes diffuse reflection in optical cavity 24. In this arrangement 32, a portion of the light reaching photodiode 18 has reflected around cavity 24 without reflecting off the surface of test patch 20. The remaining portion of the light has reflected off test patch 20 one or more times. This configuration provides the greatest immunity to surface roughness reflectivity errors since it illuminates sample 20 with light from many different directions and detects the light reflected or scattered into many different directions. As with the first arrangement 10, chamber 12 is made from, or interior surface 25 is coated with, a highly reflective non-specular material, and the diameter of opening 30 is much larger than the gap between bottom wall 36 and intermediate belt 22.

Figure 2:
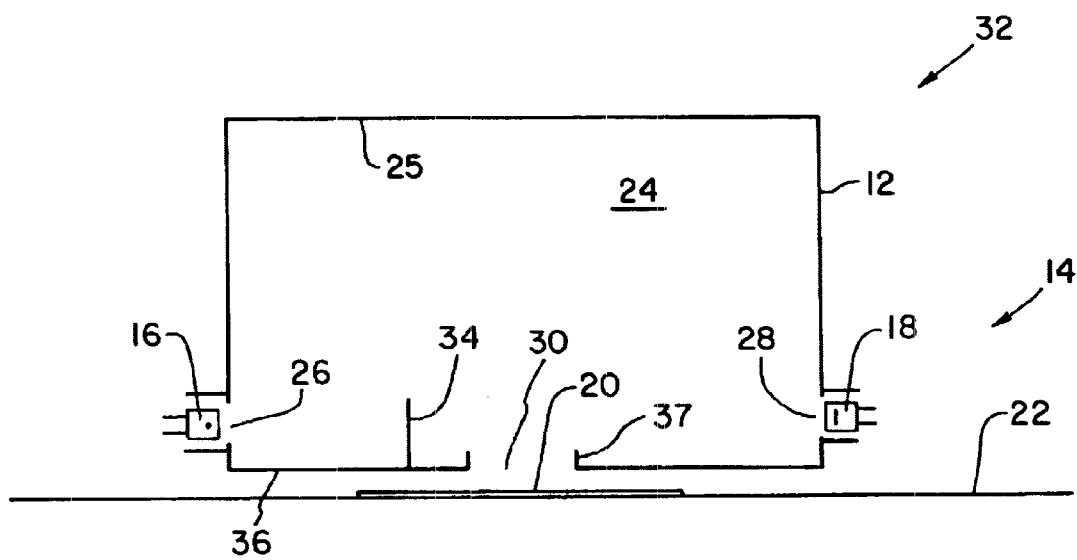
FIG. 2 is a side, sectional view of a second embodiment of a toner patch sensor arrangement of the present invention.
Figure 3:
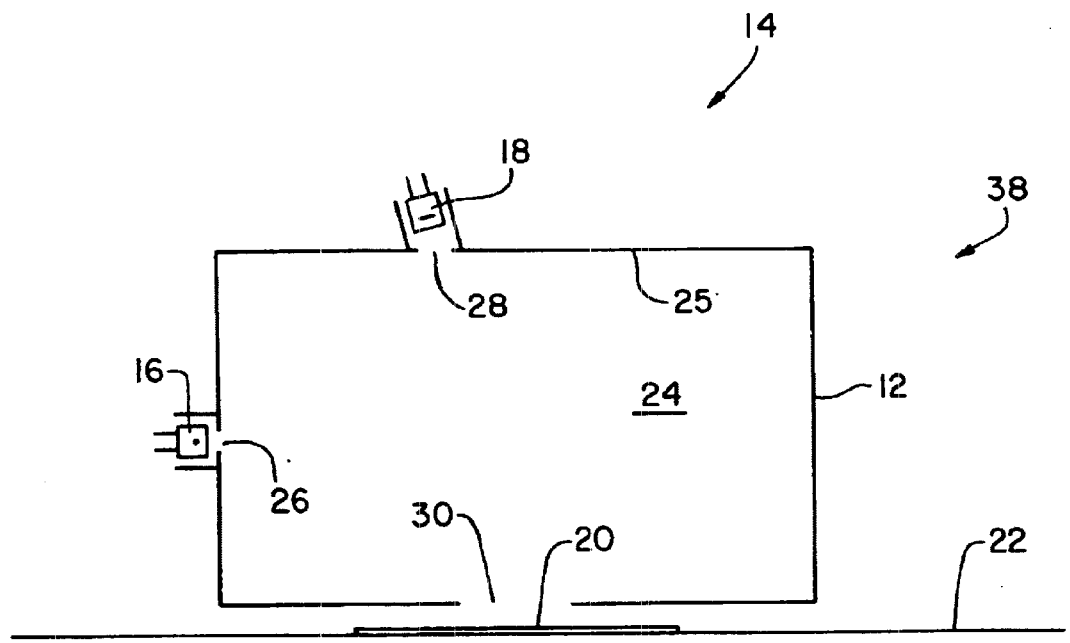
FIG. 3 is a side, sectional view of a third embodiment of a toner patch sensor arrangement of the present invention.

In the third embodiment, toner patch sensor arrangement 38 (FIG. 3), test patch 20 is diffusely illuminated as in FIG. 2, but the field of view of photodiode 18 is largely or completely limited to test patch 20. Infineon photodiode SFH203A has a limited field of view, an integral lens for focusing the collected light onto the light sensitive area, and is an example of an inexpensive photodetector that could be used as photodiode 18 in the arrangement 38 of FIG. 3.

Figure 4:
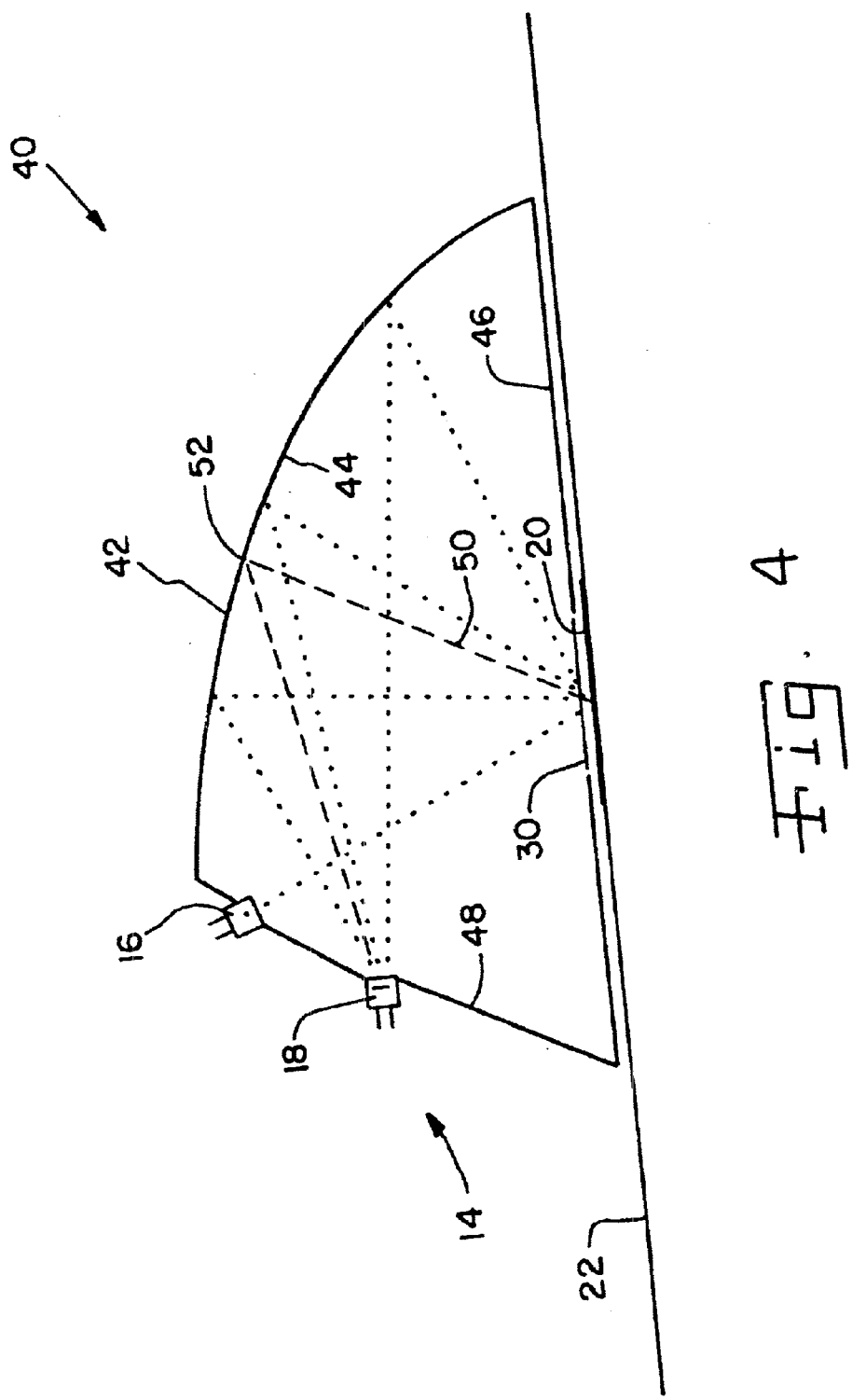
FIG. 4 is a side, sectional view of a fourth embodiment of a toner patch sensor arrangement of the present invention.

An optical cavity with specular reflecting surfaces could also be used to sample a variety of reflection directions. Specular reflection cavity surfaces can be ellipsoidal in shape. In a fourth embodiment, toner patch sensor arrangement 40 (FIG. 4), a reflector chamber 42 is ellipsoidal in shape and has test patch 20 at one focus point and photodiode detector 18 positioned at the other focus point. Chamber 40 can be molded out of acrylic and the top interior surface 44 can be aluminized to produce a high specular reflectivity. A bottom interior surface 46 is covered with black paint so as to be highly absorbing, and has an aperture 30 to allow exposure of test patch 20. A side interior surface 48 is also painted black to absorb any light which does not land on photodiode 18. Light emitting diode 16 has a narrow emission beam and photodiode 18 is a low cost Infineon photodiode BPW34 with a +/−60 degree field of view in this embodiment. The position of light emitting diode 16 allows specularly reflected light from test patch 20 to reach photodiode 18. Since the scattered light intensity tends to diminish as the scattering direction deviates from the specular direction, it is advantageous to arrange for a specularly reflected beam 50 to impinge near a center 52 of surface 44 of the elliptical mirror.

Thus, the openings for the illumination source, the test patch, and the photodiode may be configured to produce three different design scenarios: 1) direct illumination with indirect detection, 2) indirect illumination and detection, and 3) diffuse illumination with direct detection.

In the embodiments shown herein, the chambers have been shown as being hollow. However, it is to be understood that it is also possible for the cavity of the chamber to be filled with a transparent material, such as acrylic.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A toner patch sensor arrangement in an electrophotographic machine including an image bearing member having a surface, comprising:
   a chamber having a reflective interior surface, a first opening configured to expose an unfused toner patch carried by said surface of said image bearing member, a second opening and a third opening, said chamber being configured such that said first opening is proximate to said image bearing member and spaced apart from said surface of said imaging bearing member;
   a light emitting element configured to emit light onto the unfused toner patch through said first opening and said second opening; and
   a light detecting element configured to receive through said third opening light reflected off of the unfused toner patch such that at least a majority of the reflected light is received only after the light has also reflected off said interior surface of said chamber.

2. The arrangement of claim 1, wherein the light is reflected off of said interior surface before the light is reflected off of the infused toner patch.

3. The arrangement of claim 1, wherein said interior surface of said chamber comprises a specular reflecting surface.

4. The arrangement of claim 3, wherein said interior surface of said chamber is ellipsoidal in shape.

5. The arrangement of claim 4, wherein said first opening comprises a first focus point and said third opening comprises a second focus point.

6. The arrangement of claim 4, wherein said light detecting element has an angular sensitivity of +/−40 degrees.

7. The arrangement of claim 4, wherein said light emitting element is positioned such that said light detecting element receives specularly reflected light from the unfused toner patch.

8. The arrangement of claim 4, wherein light specularly reflected off of said unfused toner patch impinges on a center of said reflective interior surface.

9. The arrangement of claim 1, further comprising a baffle disposed within said chamber, said baffle being configured to reflect light received directly from said light emitting element.

10. The arrangement of claim 1, further comprising a flange at least partially defining said first opening.

11. The arrangement of claim 1, wherein said chamber is substantially hollow.

12. A toner patch sensor arrangement in an electrophotographic machine, comprising:
   a chamber having a reflective interior surface, a first opening configured to expose a toner patch, a second opening and a third opening;
   a light emitting element configured to emit light onto the toner patch through said first opening and said second opening; and
   a light detecting element configured to receive through said third opening light reflected off of the toner patch such that at least a majority of the reflected light is received only after the light has also reflected off said interior surface of said chamber, wherein the light is reflected off of said interior surface both before and after the light is reflected off of the toner patch.

13. The arrangement of claim 12, wherein said electrophotohic machine includes an image bearing member having a surface that carries said toner patch, said toner patch being unfused.

14. A toner patch sensor arrangement in an electrophotographic machine, comprising:
   a chamber having a reflective interior surface, a first opening configured to expose a toner patch, a second opening and a third opening;
   a light emitting element configured to emit light onto the toner patch through said first opening and said second opening; and
   a light detecting element configured to receive through said third opening light reflected off of the toner patch such that at least a majority of the reflected light is received only after the light has also reflected off said interior surface of said chamber, wherein said light detecting element is also configured to receive through said third opening light reflected off of said interior surface without being reflected off of the toner patch.

15. The arrangement of claim 14, wherein said electrophotographic machine includes an image bearing member having a surface that carries said toner patch, said toner patch being unfused.

16. A toner patch sensor arrangement in an electrophotographic machine, comprising:
   a chamber having a reflective interior surface, a first opening configured to expose a toner patch, a second opening and a third opening;
   a light emitting element configured to emit light onto the toner patch through said first opening and said second opening: and
   a light detecting element configured to receive through said third opening light reflected off of the toner patch such that at least a majority of the reflected light is received only after the light has also reflected off said interior surface of said chamber,
   wherein said interior surface of said chamber comprises a specular reflecting surface,
   wherein said interior surface of said chamber is ellipsoidal in shape, and
   wherein said chamber also has a first non-reflective interior surface, said first non-reflective interior surface having said first opening.

17. The arrangement of claim 16, wherein said chamber also has a second non-reflective interior surface, said second non-reflective interior surface having said third opening.

18. The arrangement of claim 16, wherein said electrophotographic machine includes an image bearing member having a surface that carries said toner patch, said toner patch being unfused.

19. A toner patch sensor arrangement in an electrophotographic machine, comprising:
   a light emitting element configured to illuminate a toner patch;
   a light detecting element configured to receive light reflected off of the toner patch; and
   an opaque element configured to intersect at least one of a first imaginary line between said light emitting element and the toner patch and a second imaginary line between said light detecting element and the toner patch.

20. The arrangement of claim 19, wherein said opaque element comprises at least one of a chamber, a baffle and a flange.

21. The arrangement of claim 19, wherein said electrophotographic machine includes an image bearing member having a surface that carries said toner patch, said toner patch being unfused.

22. A method of measuring thickness of an unfused toner patch on a surface of an image bearing member in an electrophotographic machine, said method comprising the steps of:

provoiding a chamber having a reflective interior surface, a fist opening, a second opening and a third opening;

placing said chamber over the unfused toner patch such that the unfused toner patch is exposed through said first opening, said first opening being proximate to and spaced apart from said surface of said image bearing member;

emitting light onto the unfused toner patch through said first opening and said second opening;

reflecting the light off of the unfused toner patch;

reflecting the light off of said reflective interior surface of said chamber; and detecting light reflected off of the unfused toner patch and through said third opening.

23. The method of claim 22, wherein the light is reflected off of said interior surface before the light is reflected off of the unfused toner patch.

24. The method of claim 22, wherein said chamber is substantially hollow.

25. A method of measuring thickness of a toner patch on a surface in an electrophotographic machine, said method comprising the steps of:

providing a chamber having a reflective interior surface, a first opening, a second opening and a third opening;

placing said chamber over the toner patch such that the toner patch is exposed through said first opening;

emitting light onto the toner patch through said first opening and said second opening;

reflecting the light off of the toner patch;

reflecting the light off of said reflective interior surface of said chamber; and detecting light reflected off of the toner patch and through said third opening, wherein the light is reflected off of said interior surface before the light is reflected off of the toner patch and wherein the light is again reflected off of said interior surface after the light is reflected off of the toner patch.

26. The arrangement of claim 25, wherein said electrophotographic machine includes an image bearing member having a surface that carries said toner patch, said toner patch being unfused.

27. A toner patch sensor arrangement in an electrophotographic machine, comprising:

a light emitting element configured to illuminate a toner patch;

a light detecting element configured to receive light reflected off of the toner patch; and a reflective element configured to reflect light both from said light emitting element to the toner patch and light from the toner patch to said light detecting element, wherein said electrophotographic machine includes an image bearing member having a surface that carries said toner patch, said toner patch being unfused.

* * * * *